(12) United States Patent
Green

(10) Patent No.: US 9,295,788 B2
(45) Date of Patent: Mar. 29, 2016

(54) SYRINGE WITH INTEGRATED CANNULA

(75) Inventor: Christopher Green, Cooper City, FL (US)

(73) Assignee: Anestaweb, Inc., Cooper City, FL (US)

( * ) Notice: Subject to any disclaimer, the term of this patent is extended or adjusted under 35 U.S.C. 154(b) by 1219 days.

(21) Appl. No.: 13/198,012

(22) Filed: Aug. 4, 2011

(65) Prior Publication Data

US 2012/0226239 A1 Sep. 6, 2012

Related U.S. Application Data

(60) Provisional application No. 61/464,349, filed on Mar. 4, 2011.

(51) Int. Cl.
*A61M 5/32* (2006.01)
*A61M 5/178* (2006.01)
*A61B 17/34* (2006.01)
*A61M 5/315* (2006.01)
*A61M 5/34* (2006.01)
*A61M 5/50* (2006.01)

(52) U.S. Cl.
CPC ............ *A61M 5/3291* (2013.01); *A61M 5/1782* (2013.01); *A61B 17/3417* (2013.01); *A61B 2017/3454* (2013.01); *A61M 5/31515* (2013.01); *A61M 5/345* (2013.01); *A61M 5/347* (2013.01); *A61M 5/502* (2013.01); *A61M 2005/3201* (2013.01)

(58) Field of Classification Search
CPC .......... A61M 5/1782; A61M 5/31515; A61M 5/347; A61M 5/502; A61M 5/329; A61M 5/3291; A61M 5/345; A61M 2005/3101; A61M 2005/3201; A61M 5/32; A61M 5/3286; A61B 17/3417; A61B 17/3454

See application file for complete search history.

(56) References Cited

U.S. PATENT DOCUMENTS

| | | | | |
|---|---|---|---|---|
| 3,491,757 A | * | 1/1970 | Arce | 604/242 |
| 3,638,650 A | * | 2/1972 | Burke et al. | 604/240 |
| 4,617,941 A | | 10/1986 | Ichikawa et al. | |
| 5,158,554 A | * | 10/1992 | Jepson et al. | 604/539 |
| 5,271,744 A | * | 12/1993 | Kramer et al. | 604/506 |
| 6,165,153 A | | 12/2000 | Kashmer | |
| 6,511,472 B1 | * | 1/2003 | Hayman et al. | 604/533 |
| 6,524,278 B1 | * | 2/2003 | Campbell et al. | 604/192 |
| 7,351,228 B2 | | 4/2008 | Keane et al. | |
| 7,534,233 B2 | | 5/2009 | Schiller et al. | |
| 2009/0299325 A1 | * | 12/2009 | Vedrine et al. | 604/414 |

* cited by examiner

*Primary Examiner* — Bhisma Mehta
*Assistant Examiner* — Larry R Wilson
(74) *Attorney, Agent, or Firm* — Malin Haley DiMaggio & Bowen, P.A.

(57) ABSTRACT

A syringe assembly includes a tubular barrel having an open proximal end, a distal end, and an internal a fluid retaining chamber. A plunger is slidingly received in the chamber and is configured to draw fluid into and expel fluid from the chamber. A hollow projection extends from the distal end of the barrel and a cannula extends from the hollow projection. The cannula may have a spiked tip, a transverse orifice, and longitudinally disposed bi-lateral fluid flow channels. The cannula is adapted to penetrate the seal of a medical access point, such as a medicine vial, IV port, or catheter port. A receiving collar including one or more male threads surrounds the hollow projection and the cannula and is adapted to releasably engage a needle hub. The needle hub has an internal cavity configured to matingly receive and cover the cannula.

18 Claims, 13 Drawing Sheets

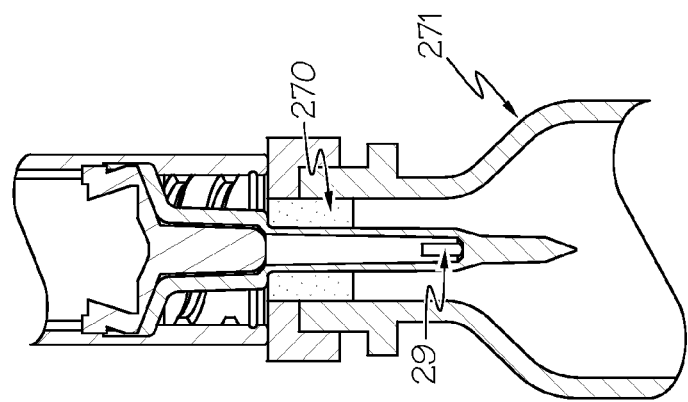
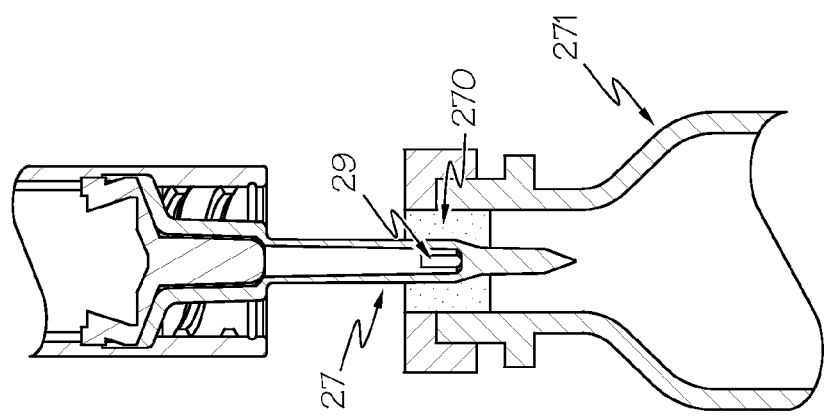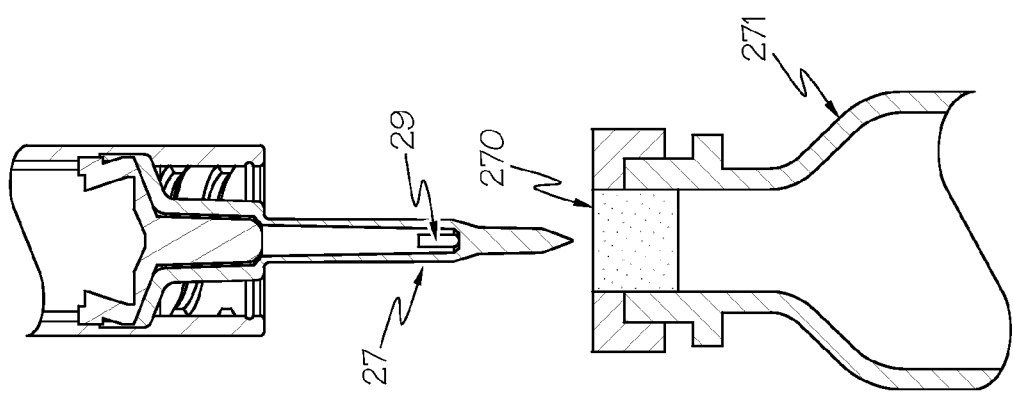

SYRINGE WITH INTEGRATED CANNULA

CROSS REFERENCE TO RELATED APPLICATIONS

This application claims the benefit of U.S. Provisional Application No. 61/464,349, filed Mar. 4, 2011.

STATEMENT REGARDING FEDERALLY SPONSORED RESEARCH OR DEVELOPMENT

N/A

BACKGROUND OF THE INVENTION

1. Field of the Invention

The present invention generally relates to medical devices for the administration of medicines, drugs, and other therapeutic materials and more specifically to a syringe having an integrated cannula and components related thereto.

2. Description of Related Art

In the early stages of syringe use, medical professionals relied on reusable glass hypodermic syringes and needles which were boiled for sterility after each use. Although accomplishing the goal of delivering medication into the human body in a sterile manner, these early glass syringes were relatively cumbersome and crude in design. As early as the 1950's, the idea for a disposable syringe came to pass. With the development of new materials, the plastic disposable syringe was a great advancement providing increased disease prevention over prior designs.

Today, the most common plastic disposable syringe comprises a syringe barrel having an internal chamber and a plunger rod disposed in the chamber which can either draw fluid into the chamber, or expel fluid from the chamber. Typically, the tip of the syringe includes a hollow tubular projection or nozzle encompassed by a threaded outer circular structure, sometimes referred to as a "Luer lock" or a "Luer slip," that is adapted to engage with a needle hub or other device that has a hub (i.e. Luer fitting) configured to mate with the circular structure. For purposes of hypodermic injections, the needle hub typically has a hypodermic needle of varying length that is in fluid flow communication with the chamber of the syringe when joined to the barrel.

In a typical setting, more than one needle hub is required to carry out an injection operation. First, a draw-needle hub having a relatively large-bore steel needle must be attached to the syringe, which draw needle is then inserted into a medicine container. In some cases, the medicine container has a pre-slit rubber septum allowing for easier access. In any event, the plunger rod is pulled outward, drawing the medicine from the container, through the draw needle, and into the chamber. At that point, the technician must then remove the draw needle hub from the container, detach the hub from the syringe and set it aside, and then attach an injection-needle hub that has a relatively small-bore hypodermic needle back onto the syringe. Finally, the injection can be carried out. This multi-step procedure has several disadvantages. For one, the technician must remove and replace the draw-needle hub with the injection-needle hub which can compromise overall sterility of the procedure while also exposing the technician and patient to the risk of needle sticks from the draw-needle hub that is set aside. Additionally, confusion could occur between the two needle hubs, causing the technician to inadvertently inject the patient using the large-bore and presumably less sterile draw needle. The overall procedure is generally cumbersome in that it requires the technician to interact with several different components, i.e. syringe, draw hub, injection hub, medicine vile, etc. Finally, because the syringe and its various needle hubs are disposable, a standard injection procedure requiring at least two different needle hubs can become exceedingly expensive over time.

There have been numerous attempts to develop improved medical syringes; however, none adequately solve the shortcomings outlined above.

For example, U.S. Pat. No. 5,158,554 to Jepson et al. describes a syringe having a cannula configured to be received in a pre-slit injection site such as an IV (intravenous) entry path. Included is a housing having a pre-slit septum adapted to receive a blunt cannula having a locking member. The locking member is adapted to latch to the injection site forming a mechanically coupled unit with the housing. The cannula is designed to engage a male-threaded Luer-lock of the syringe such that the cannula is removable and replaceable with an injection needle hub or the like.

U.S. Pat. No. 6,165,153 to Kashmer describes a single-use syringe assembly including an elongated syringe barrel receiving a plunger rod having a plunger tip. The syringe barrel has a nozzle at its closed end formed to receive the plunger tip. The distal end of the nozzle contains an annular inward biased ring adapted to mate with a locking detent on the plunger tip. Upon usage, when the plunger reaches its full range of motion inward, the locking detent is irreversibly matted with the nozzle inwardly biased ring, thereby preventing the reuse of the syringe assembly. The distal end of the syringe includes a Luer-type threaded needle mount that is adapted to receive a variety of draw and injection needle assemblies or other Luer-type hubs.

U.S. Pat. No. 7,351,228 to Keane et al. describes an arterial blood collection syringe having a self-sealing filter provided at the front end of the plunger rod. Vents are spaced radically about the front end of the plunger. The plunger is received in a syringe barrel which barrel has a fitting at its distal end adapted to receive a variety of needle hubs including a draw-needle hub and a hypodermic injection-needle hub.

U.S. Pat. No. 7,534,233 to Schiller et al. describes an IV flush syringe assembly having a barrel with an inside chamber for retaining fluid, an open proximal end and a distal end including a distal wall with an elongate tip extending distally therefrom having a passageway in fluid communication with the chamber. A plunger is disposed in the chamber. An anti-reflux structure is disposed in the barrel for controlling plunger-stopper deflection when the fluid has been delivered from the chamber wherein the stopper is on contact with structure on the distal wall of the chamber. A needle assembly is configured to removably attach to the distal end of the barrel wherein the assembly includes hub attached to a needle or blunt cannula.

Becton, Dickinson and Company markets a product under its BD Medical brand called the "BD Twinpak" which includes a syringe having a standard Luer-lock type fitting adapted to releasably receive a specialized hub having a "blunt plastic cannula." The removable plastic cannula is limited to split-septum access in connection with BD's IV receptacles. The "Twinpak" also includes a "red hub filling device" which includes a draw-needle which is needed in order to fill the syringe prior to fitting it with the blunt plastic cannula. Accordingly, the technician must first use the red hub filling device to draw medicine into the syringe and then remove and replace it with the blunt plastic cannula for subsequent IV access.

Despite some improvements, each of the devices described above still relies on a separate draw-needle hub in order to fill the chamber of the syringe, and the technician must still swap out the draw-needle hub with an injection hub (whether a needle-based or needleless, in the case of the BD Twinpak) before an hypodermic injection or other medicine delivery (e.g. IV or catheter port) procedure can be completed. Thus, these improved devices still have all of the disadvantages associated with traditional disposable syringes outlined above. With that in mind, there is a definitive need for a syringe assembly and system that completely eliminates the need for large bore draw-needles and hubs while also eliminating the multi-step injection procedure associated therewith.

It is, therefore, to the effective resolution of the aforementioned problems and shortcomings of the prior art that the present invention is directed. However, in view of the syringe assemblies in existence at the time of the present invention, it was not obvious to those persons of ordinary skill in the pertinent art as to how the identified needs could be fulfilled in an advantageous manner.

SUMMARY OF THE INVENTION

The present invention provides a syringe assembly that includes a tubular barrel having an open proximal end, a distal end, and an internal surface delimiting a fluid retaining chamber. A plunger is slidingly received in the chamber and is configured to draw fluid into the chamber and to expel fluid out of the chamber. A cannula extends from and is integrated with the distal end of said barrel and is in fluid flow communication with the chamber. In some embodiments, the barrel of the syringe assembly also includes a hollow protrusion extending from the distal end of said barrel, which protrusion delimits a base for the cannula.

In some embodiments, the cannula includes a transverse orifice in fluid flow communication with the chamber. Further, the cannula further includes bi-lateral fluid flow channels disposed longitudinally on the cannula, which channels are in fluid flow communication with the orifice. In some embodiments, the cannula includes a spiked tip adapted to penetrate a seal of a medical access point such as a pre-slit or non-slit flexible septum or other seal found on a medicine vial, IV access port, catheter access port, or other medicine delivery access point or injection receptacle known in the field.

A receiving collar surrounds at least a portion of the cannula and is adapted to receive an attachment hub, such as a needle hub. In some embodiments, the receiving collar includes one or more male threads, which may be of the Luer-lock or Luer-slip type. A exemplary attachment hub, such as a hypodermic injection-needle hub includes an internal cavity configured to matingly receive the cannula when the hub is placed over the cannula and received in the receiving collar of the barrel. The hub also includes a distal aperture which may receive a hypodermic needle or other structure. Further, in some embodiments, the outer surface of the hub includes one or more longitudinal fins which facilitate manual attachment and detachment of said hub from the receiving collar.

In some embodiments, the receiving collar of the barrel receives an adapter hub including a nozzle extending distally from the flange of the hub, and a shield disposed around the nozzle, wherein an internal space of the nozzle is configured to receive the cannula, and wherein the nozzle is in fluid flow communication with the cannula. The adapter hub is configured to cover the cannula and convert the syringe assembly into a standard Luer-type syringe which can then receive other standard needle hubs or other attaching devices known in the art. Accordingly, an internal surface of the shield of the adapter hub delimits a secondary receiving collar for releasably retaining these other hubs.

Accordingly, it is an object of the present invention to provide a novel syringe assembly that includes an integrated cannula to provide needleless access to a variety of medicine delivery access points without the need for a removable draw needle or draw-needle hub.

It is another object of the present invention to provide a syringe assembly including an integrated cannula surrounded by a receiving collar wherein the receiving collar receives a hub having an internal cavity adapted to receive the cannula and provide additional functionality, such as hypodermic needle compatibility.

It is another object of the present invention to provide a syringe assembly including an integrated cannula in order to eliminate the need for multiple hubs which would otherwise be required in order to carry out a standard hypodermic injection procedure.

It is yet another object of the present invention to provide a syringe assembly including a spiked cannula for penetrating a variety of seals found on medicine vials or other delivery access points, including pre-slit or non-slit septums.

It is yet another object of the present invention to provide a syringe assembly configured to receive an adapter hub that converts the syringe assembly into a standard Luer-type syringe, providing legacy compatibility with needle hubs and other attaching devices presently available in the field.

It is yet another object of this present invention to provide a syringe assembly configured to permanently lock its plunger rod in place after delivering the dosage of medication, which prevents the re-use of contaminated syringes.

It is yet another object of the present invention to provide a syringe assembly that eliminates the need for large bore draw needles and, in turn, provides a cost effective, simple, safe, and sterile syringe solution.

In accordance with these and other objects which will become apparent hereinafter, the instant invention will now be described with particular reference to the accompanying drawings.

BRIEF DESCRIPTION OF THE DRAWINGS

FIGS. 8A-8C depict the cannula of the present syringe assembly in various stages of insertion into a medicine delivery access point.

DETAILED DESCRIPTION

Figure 1:
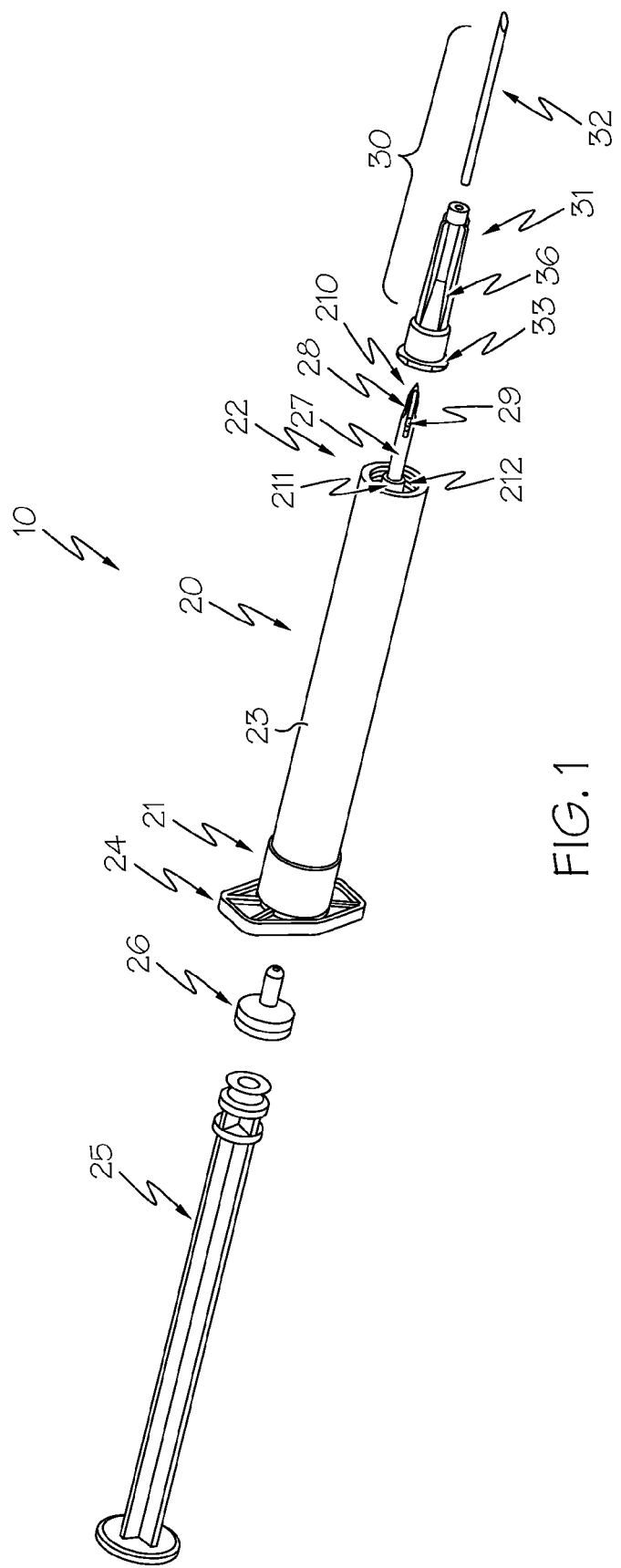
FIG. 1 is a disassembled perspective view of one embodiment of the present syringe assembly.

With reference to FIGS. 1-4, shown is one embodiment of the syringe 10 of the present invention. Shown is an elongated tubular syringe barrel 20 having an open proximal end 21 and a partially closed distal end 22. The interior surface of barrel 20 delimits a chamber 23. Disposed at proximal end 21 is a finger guard 24 which extends laterally from the outer surface of barrel 20. Plunger 25 is slidingly received in the chamber 23 and is configured to reciprocate therein. Plunger tip 26 may be disposed at the distal end of plunger 25, providing a liquid-tight sealed engagement with chamber 23. The finger guard 24 is configured to assist with compressing plunger 25 into chamber 23 during use.

Figure 3:
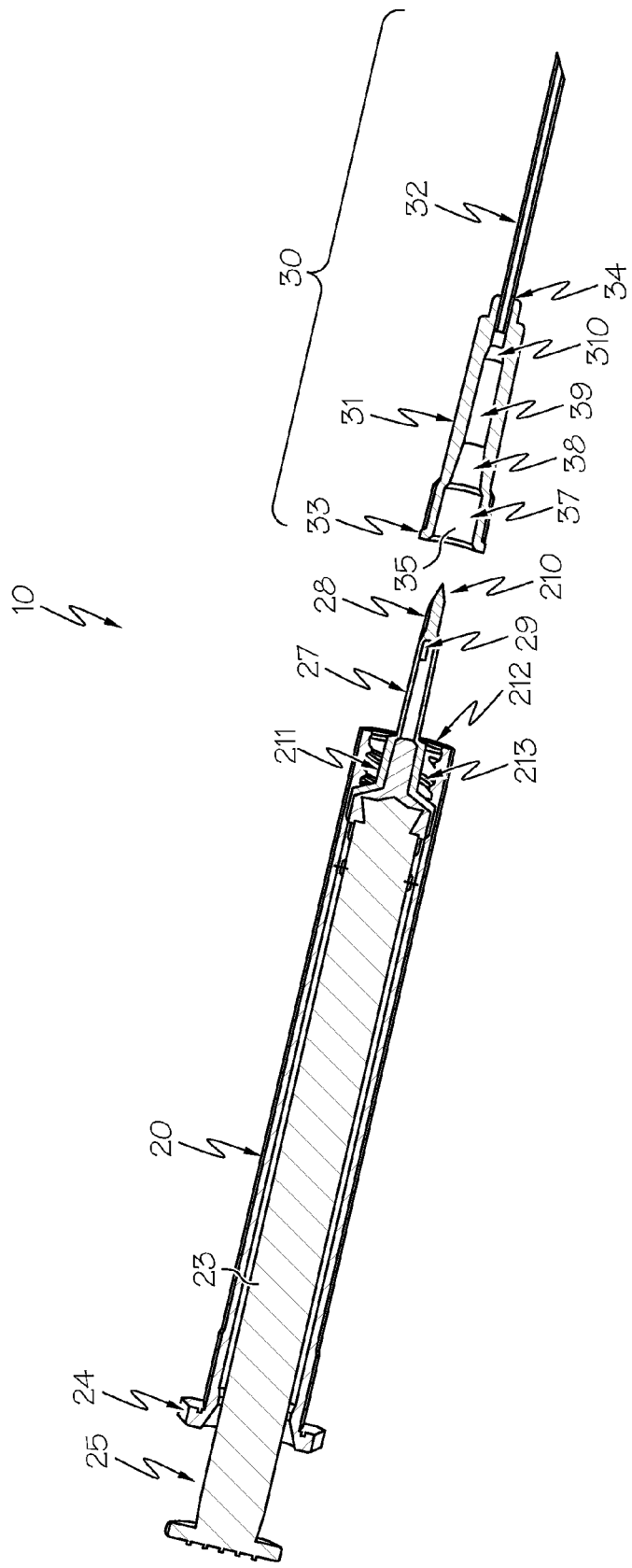
FIG. 3 is a partially assembled sectional view of the present syringe assembly.
Figure 4:
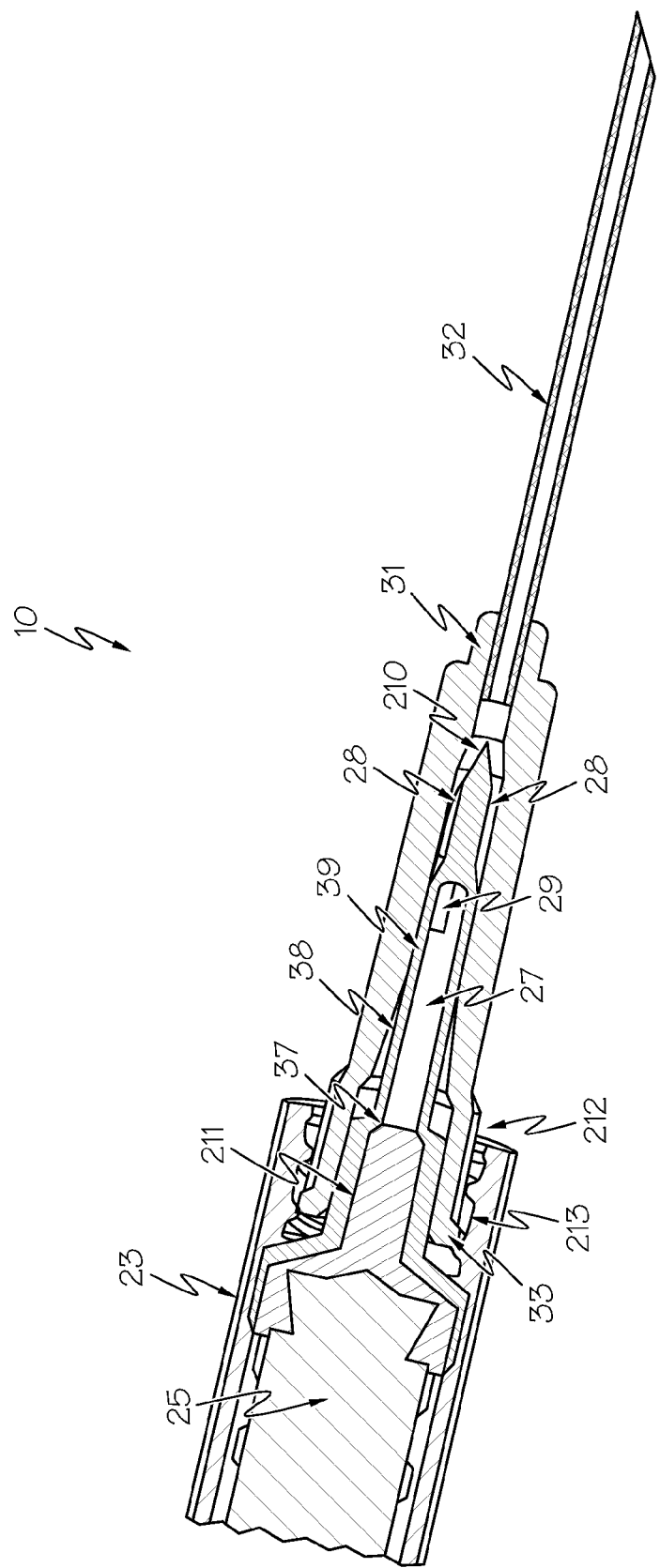
FIG. 4 is a fully assembled sectional view of the present syringe assembly.
Figure 7:
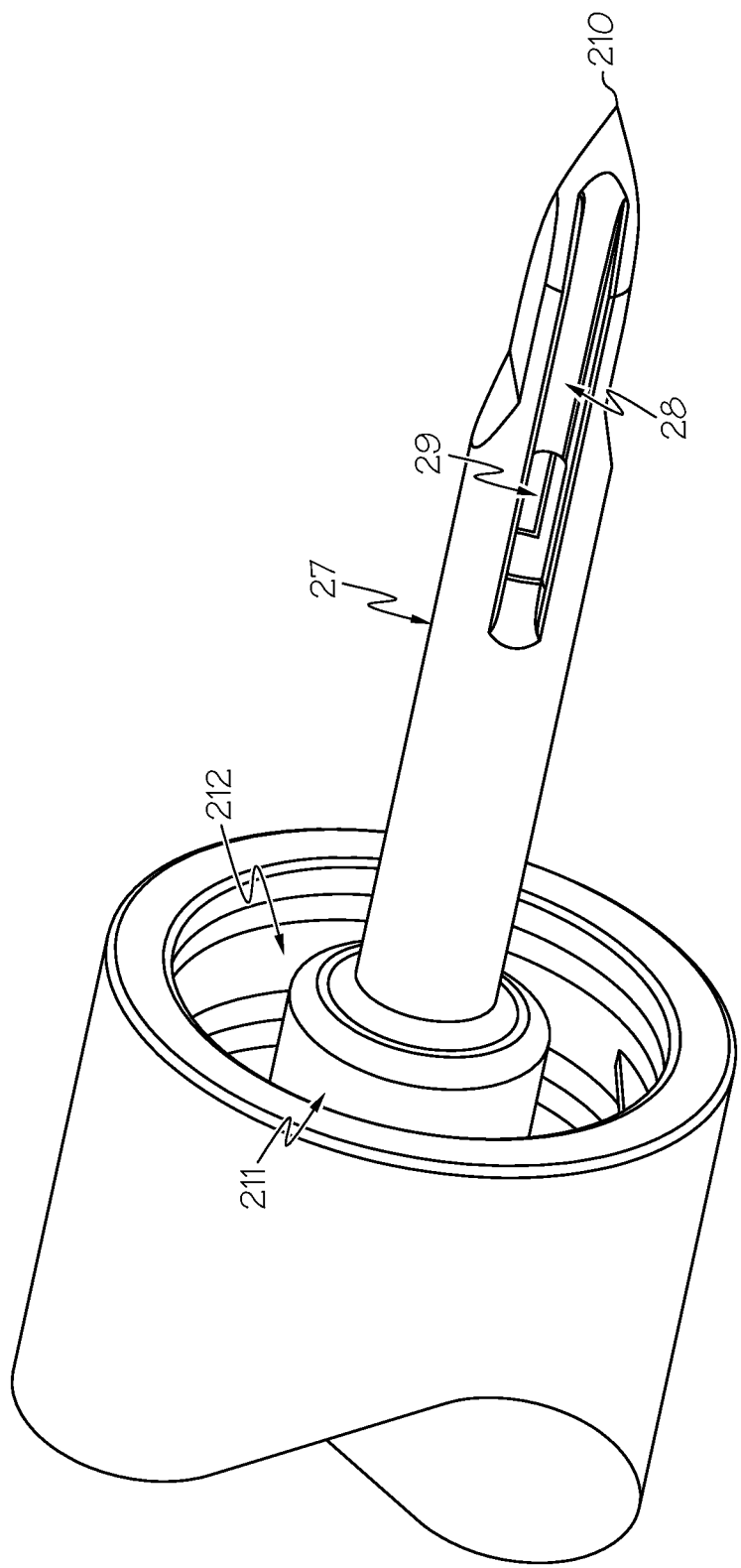
FIG. 7 is a close-up perspective view of one embodiment of the cannula integrated into the present invention

Extending from and integrated into the distal end 22 of barrel 20 is a cannula 27. Cannula 27 delimits a hollow lumen that is in fluid flow communication with chamber 23 of barrel 20. As more clearly shown in FIG. 7, in some embodiments, cannula 27 includes bi-lateral fluid flow channels 28 disposed longitudinally on either side of the cannula. Further, cannula 27 includes a fluid orifice 29 which is provided transversely through the body of cannula 27 and in flow communication with channels 28. In some embodiments, cannula 27 includes a spiked tip 210, although the tip 210 could also be slant-cut or blunt. In some embodiments, as shown in FIGS. 1, 3 & 4, the distal tip 210 is closed. Further, cannula 27 is integrated and coextensive with a slightly larger hollow protrusion 211 which delimits the base for cannula 27 with respect to barrel 20. Surrounding at least a portion of, and spaced-apart from cannula 27 is a distal receiving collar 212 which defines a threaded attachment point for needle hubs or other attaching devices, which will be discussed in detail below. In some embodiments, receiving collar 212 is generally of the Luer-lock type, having at least one male thread 213 extending from the surface of collar 212. In some embodiments, collar 211 may be generally of the Luer-slip type as is known in the art. Collar 212 may have other engagement means as are generally known and used in the art.

Integrated cannula 27 provides needleless access to a variety of known medicine delivery access points known in the medical field, many of which would normally only be accessible by way of a large-bore steel draw needle. For example, cannula 27 may provide access to a pre-slit rubber septum found on any number of single or multi-dose medicine vials, IV ports, catheter ports, or other medicine delivery access points and injection receptacles. With cannula 27 having a spiked tip 210, it is capable of piercing a variety of non-split membranes or other closure means that seal single or multi-dose medicine vials, IV ports, catheter ports, or other access points and injection receptacles. With chamber 23 in fluid flow communication with protrusion 211 and cannula 27, it is appreciated that cannula 27 is useful for drawing fluids from the aforementioned access points into the chamber 23 while also being useful for expelling fluids from chamber 23 into such access points. By providing a syringe 10 having an integrated and continuous cannula 27, the present invention eliminates the need for external and unsafe large-bore draw needle hubs and provides a unitary, integrated medicine delivery access point solution.

By way of non-limiting example, cannula 27 is compatible with and can provide access to the following known medical access points: Becton-Dickinson "Q-Syte" and "Posiflow"; B. Braun "SAFELINE" and "ULTRASITE"; Hospira "LifeShield Prepierced," "CLAVE," "MicroCLAVE," and "CLC2000"; Alarais "VerasaSafe," "Smartsite," and "Smartsite Plus'" Baxter "Interlink Site" and "Clearlink," Teva "TEVADAPTOR, Maximus "MaxPlus; and Rymed InVision-Plus. Cannula 27 can provide access to other needle-based and needleless access points known in the art but not specifically mentioned herein. Cannula 27 also reduces the need for pre-split multi-dosage vial adapters. Because of its universal nature, the present invention can be adopted by hospitals and other health care providers without a change in existing protocols for vial, IV, catheter, or other medicine delivery systems.

It is further appreciated that the access points identified herein vary in dimension and depth. However, the cannula 27 of the present invention is universally compatible with these devices because of the arrangement of orifice 29 and bi-lateral fluid flow channels 28. For example, many of the access points will have a septum or other membrane or seal that is shallow enough to allow orifice 29 to penetrate completely beyond the seal, allowing the medicine to flow directly into (or out of, in the case of an fluid expulsion) the orifice 29. On the other hand, if the access point seal is substantially deeper than the length between the base of cannula 27 and orifice 29, the bi-lateral fluid flow channels 28, which are distal from the orifice 29, will provide a passageway to orifice 29 for the medicine to flow into (or out of). FIGS. 8A-8C show an example of cannula 27 being inserted into a seal or septum 270 of a medicine vial 271. Further still, a removable extension valve may be provided which is attachable on one end to the medicine vial or other delivery access point and includes a cylindrical body having a depth configured for receiving the entirety of cannula 27 in a manner to provide optimal fluid flow thereto.

In addition to providing needleless access to a variety of medicine delivery ports and systems via cannula 27, syringe 10 is also configured to receive a variety of needle hubs and other access devices which are needed for hypodermic injections or other similar procedures. For example, shown in FIGS. 1-4 is needle assembly 30 including a hub 31 and a hollow needle 32 which assembly is adapted to releasably engage the receiving collar 212 of barrel 20. The proximal end of hub 31 includes a flange 33 which may be of the Luer-lock or Luer-slip type that is configured to engage thread 213 of receiving collar 212. The distal end of hub 31 includes an aperture 34 which is dimensioned to receive needle 32. It is understood that needle 32 can be a hypodermic or other needle of any length and gauge, provided that hub 31 and aperture 34 are dimensioned appropriately. For example, the present invention contemplates compatibility with needle hubs 31 having needles 32 between 14 g and 30 g.

Hub 31 further includes an internal cavity 35 which is dimensioned and configured to receive cannula 27 when needle assembly 30 is provided on barrel 20. With chamber 23 in fluid flow communication with cannula 27, the engagement of needle assembly 30 over cannula 27 places cannula 27 in fluid flow communication with hub 31 and, in turn, needle 32. In some embodiments, hub 31 has one or more longitudinally disposed fins 36 extending from the outer surface thereof which facilitates manual rotation of the hub 31 during attachment to receiving collar 212.

FIG. 3 is a longitudinal cross-section view of syringe 10 showing plunger 25 completely disposed within chamber 23. In some embodiments, the plunger tip 26 is configured such that its geometry precisely mates with the internal structure of protrusion 211 which eliminates dead space and assures that the entire contents of chamber 23 is expelled therefrom through cannula 27 during operation. Also shown is needle assembly 30 with needle 32 attached to the distal end of hub 31. The internal cavity 35 of hub 31 is dimensioned to receive and matingly engage protrusion 211 and cannula 27. Accordingly, internal cavity 35 includes a proximal conical section 37 which steps down to an intermediate conical section 38 which steps down a cylindrical section 39, terminating at tip 310. Tip 310 is open at aperture 34 which is coextensive with the lumen of needle 32. Tip 310 is specifically dimensioned to receive tip 210 of cannula 27 in order to provide an optimal fluid flow engagement.

Figure 2:
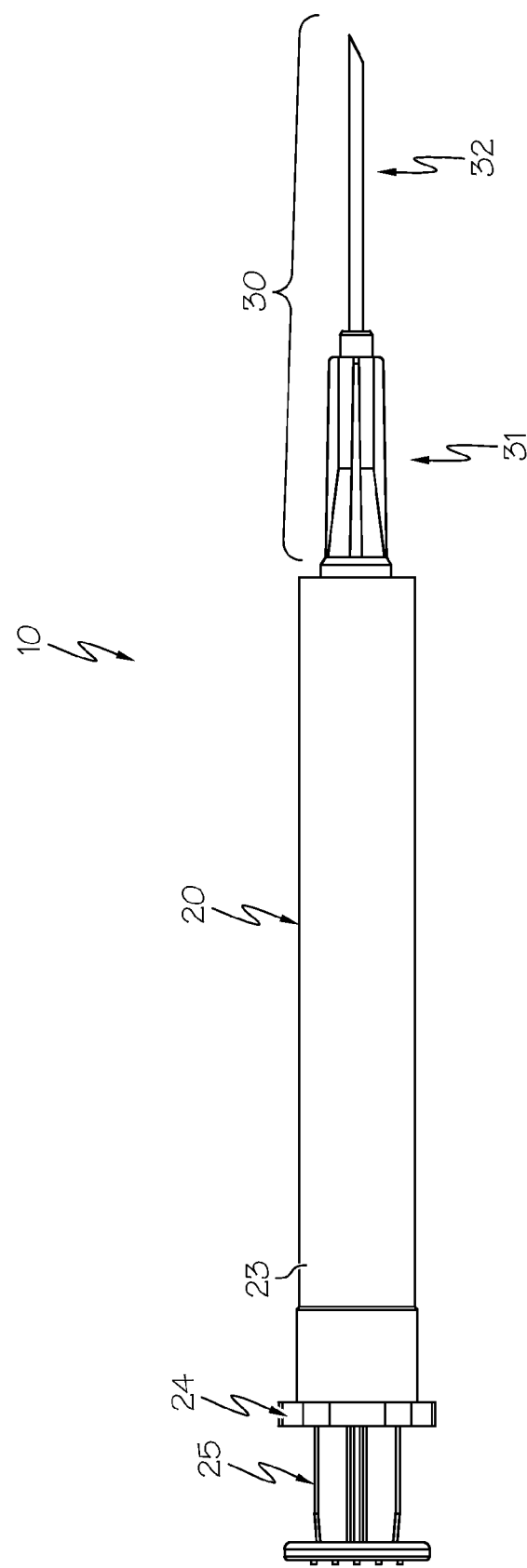
FIG. 2 is a fully assembled side view of the present syringe assembly.

FIG. 2 is a side view of the syringe 10 in its fully assembled state, showing needle assembly 30 attached to the barrel 20 and plunger 25 fully disposed within chamber 23. As shown, needle assembly 30 completely encompasses the distal structure of barrel 20 including protrusion 211 and cannula 27. FIG. 4 is a sectional view of the syringe 10 shown in FIG. 3, which more clearly shows the engagement of the various components. When fully threaded about threads 213, flange 33 is seated substantially toward the bottom of receiving collar 212 and is locked in place. In this sectional view, the fluid flow path is more clearly seen. When one desires to provide fluid from syringe 10 such as during an injection procedure, plunger 25 is pressed into chamber 23 causing fluid from chamber 23 to be expelled through protrusion 211 into cannula 27, through orifice 29, across bi-lateral channels 28, and then through the lumen of needle 32, finally exiting the needle 32.

Figure 5:
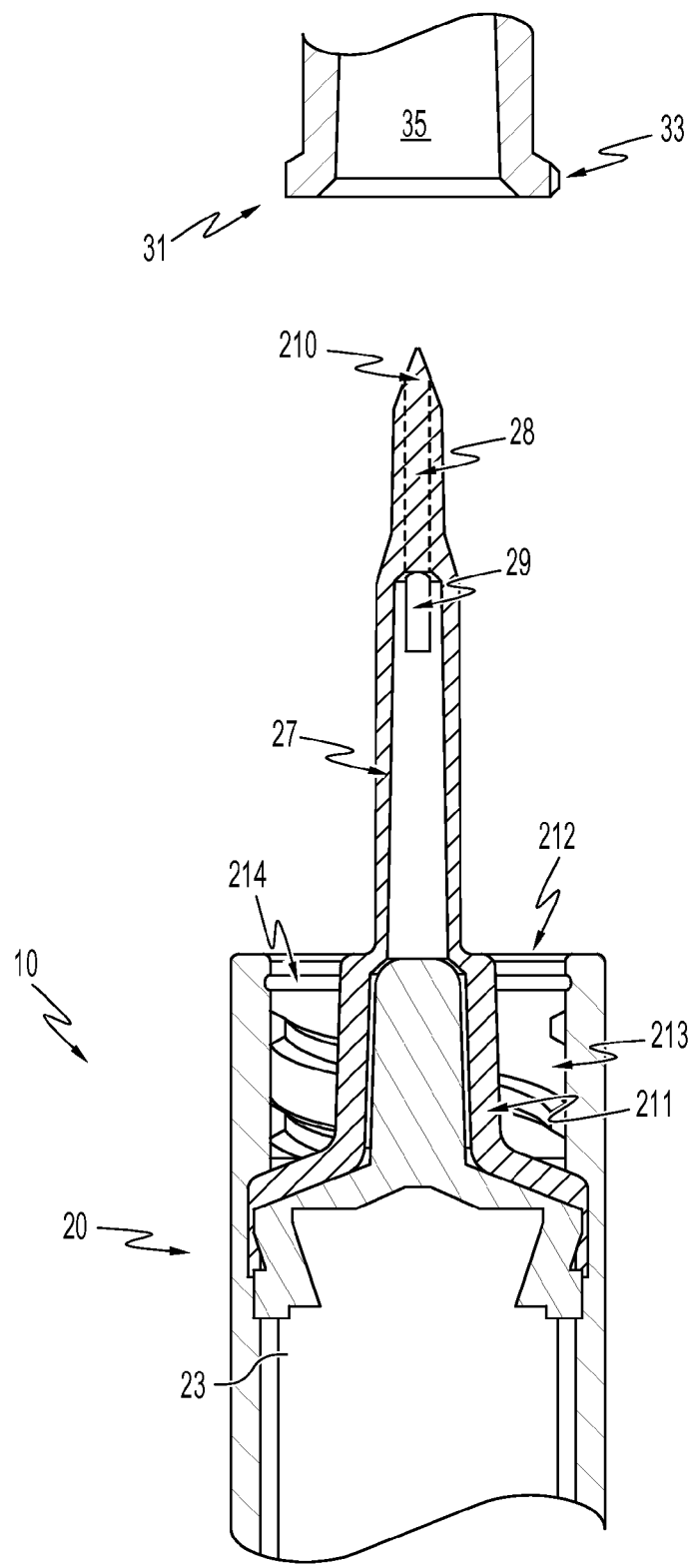
FIG. 5 is a partially assembled close-up view of the distal end of the present syringe assembly.
Figure 6:
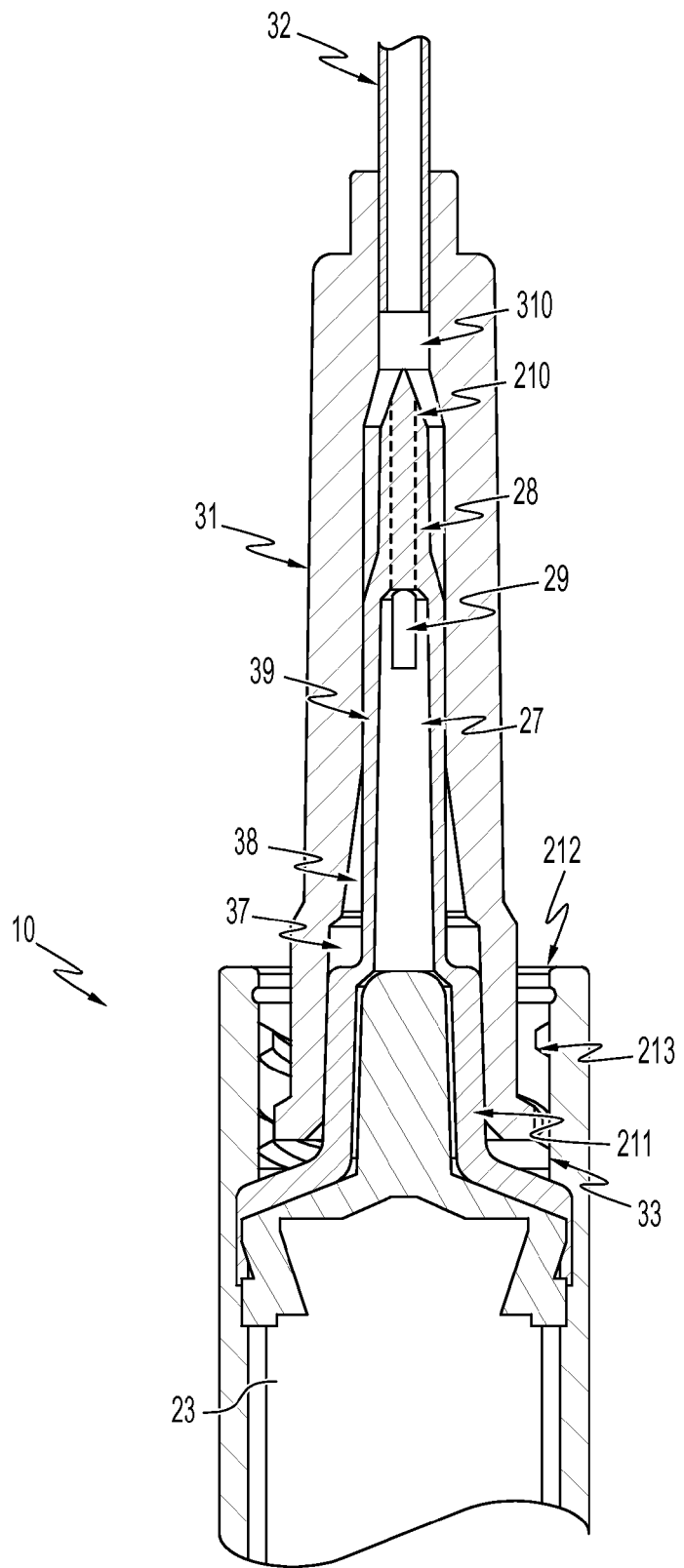
FIG. 6 is an assembled close-up view of the distal end of the present syringe assembly.

The bi-lateral fluid flow channels 28 facilitate fluid flow from orifice 29 across tip 210. FIGS. 5 and 6 show a more up-close view of the structure of the present invention and the engagement of needle assembly 30 to barrel 20. In some embodiments, cannula 27 fits snugly inside cylindrical section 39 of cavity 35, so as to form a fluid-tight seal which assures that the fluid is completely expelled out of cannula 27. Because of the fitted engagement of internal cavity 35 around cannula 27, the syringe 10 of the present invention results in substantially less residual medicine volume as compared to standard syringe/hub engagements known in the art. By leaving less residual medicine or bodily fluids in the syringe 10, there is less waste of medicine, reducing costs. Additionally, there is less volume of contaminated bodily fluids, therefore reducing the spread of contagious pathogens and significantly reducing the spread of disease.

It is appreciated that the present invention is intended to provide a universal syringe that can receive a variety of needle hubs or other like attachments that are not specifically designed to be received over cannula 27. Many of the presently available standard Luer-type needle hubs lack an internal cavity that is large enough or dimensioned correctly to fit over cannula 27 and still engage receiving collar 212. Accordingly, the present invention provides an adapter hub 40, as shown in FIGS. 9-12, which increases the overall universal compatibility of the present invention. Adapter hub 40 includes a proximal flange 41, an intermediate cylindrical shield 42, and a nozzle 43. The flange 41 may be of the Luer-lock or Luer-slip type and is configured to engage thread 213 of receiving collar 212. The proximal portion of adapter hub 40 transitions distally into nozzle 43, which is a hollow tubular projection having an internal space dimensioned to receive cannula 27. Shield 42 extends from the proximal portion and is disposed around at least a portion of nozzle 43, terminating slightly before the distal end of nozzle 43 and providing protection for same.

Figure 9:
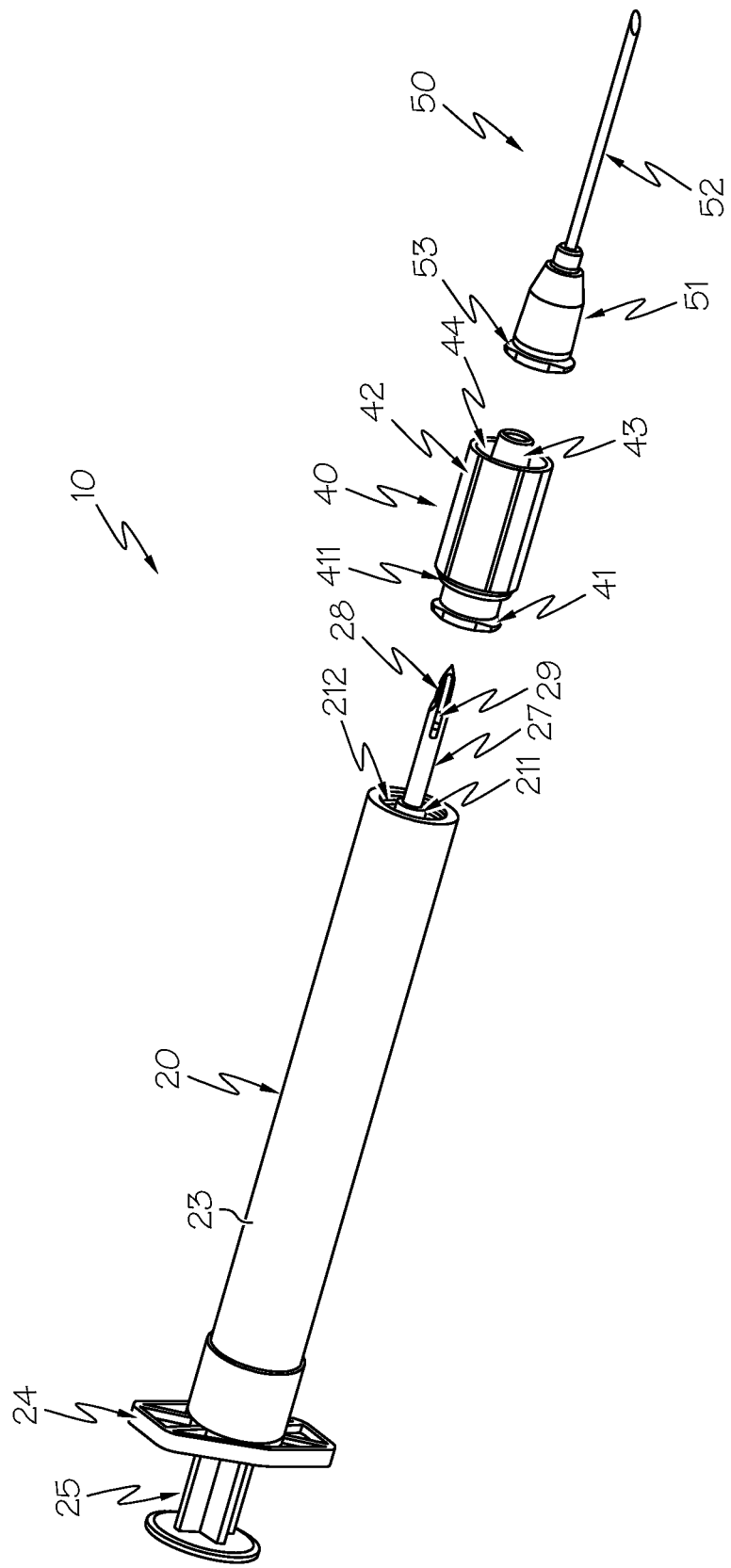
FIG. 9 is a disassembled perspective view of another embodiment of the present syringe assembly, having an adapter hub.
Figure 10:
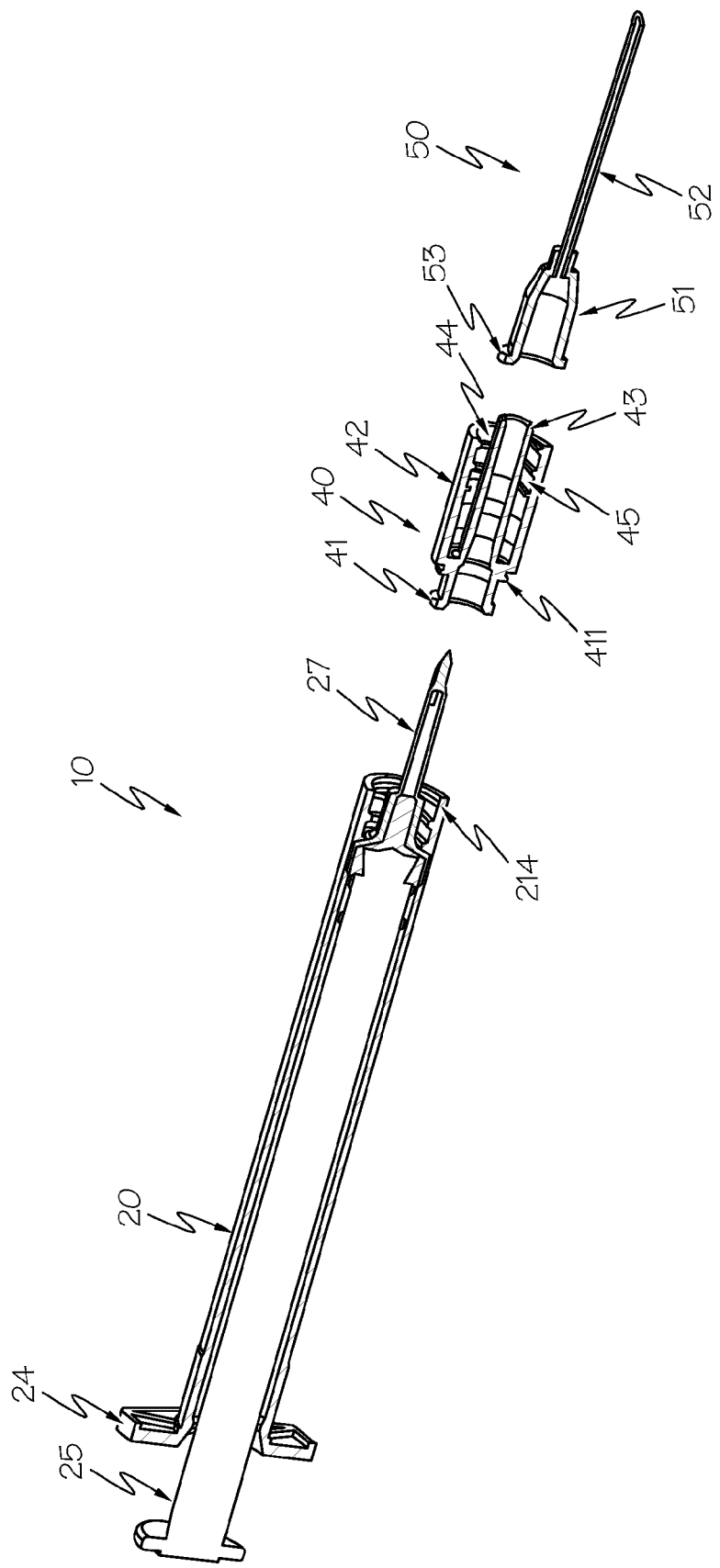
FIG. 10 is a disassembled sectional view of the present syringe assembly, having an adapter hub.
Figure 11:
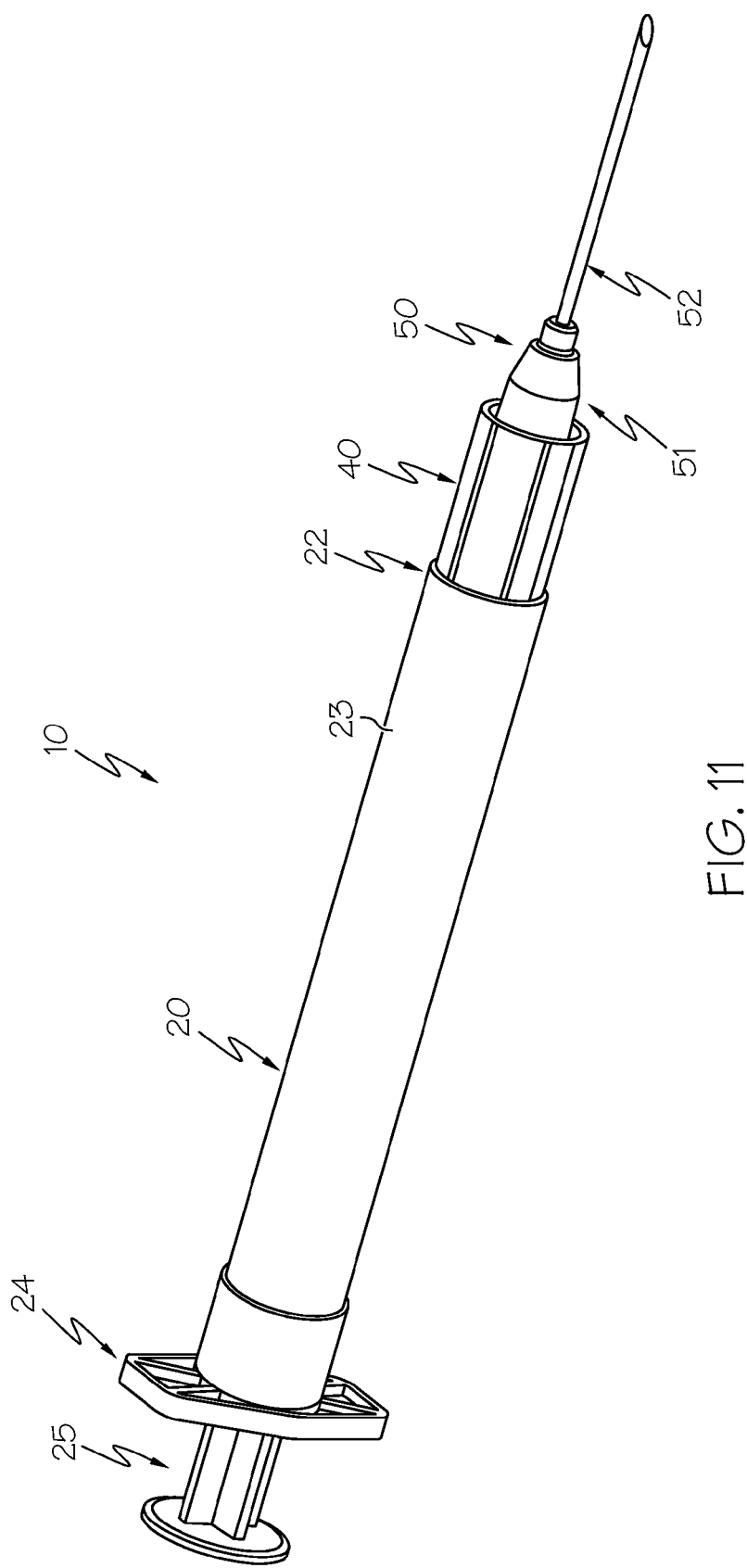
FIG. 11 is an assembled perspective view of the present syringe assembly, having an adapter hub.
Figure 12:
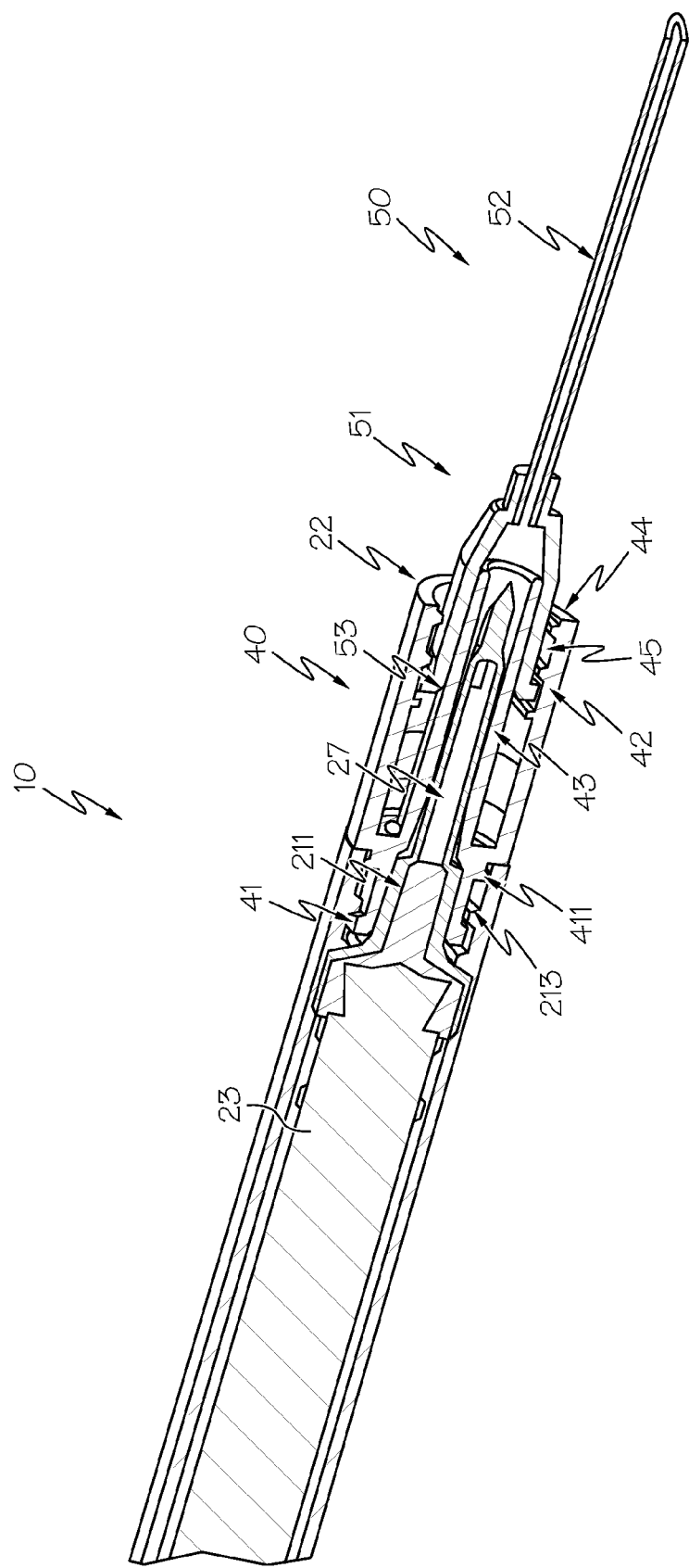
FIG. 12 is an assembled sectional view of the present syringe assembly, having an adapter hub.

At least a portion of the interior surface of shield 42 delimits a secondary receiving collar 44. In some embodiments, secondary receiving collar 44 is generally of the Luer-lock type, having at least one male thread 45 extending from the surface of collar 44. In some embodiments, collar 44 may be generally of the Luer-slip type as is known in the art. Secondary receiving collar 44 is adapted to receive a variety of attachment hubs know in the art including, but not limited to, needle hub 50 shown herein (FIGS. 9, 11). Needle hub 50 includes a hub 51 and a needle 52, hub 51 having a proximal flange 53 of the Luer-lock type which engages threads 45 of collar 44. Adapter hub 40 may also include a securing protrusion 411 which is distal from flange 41 and at the base of shield 42 (See FIGS. 9, 10, 12). Protrusion 411 is adapted to snap-fit into securing groove 214 (FIGS. 5, 10) which is at the edge of receiving collar 212 and, in some embodiments, is coextensive with thread 213. The protrusion-groove engagement is intended to keep adapter hub 40 secured to the distal end 22 of barrel 20 when attaching or removing a hub 50 to/from secondary receiving collar 44. Thus, it is preferred that the force needed to break the protrusion-groove engagement is greater than the force needed to disengage (by twisting) the flange 53 from the thread 45 of receiving collar 44. It is appreciated that adapter hub 40 serves at least two purposes. First, adapter hub 40 converts the fittings of barrel 20 such that it has a more usual Luer-type fitting arrangement, namely collar 44 so that the syringe 10 maintains its compatibility with known needle hubs and other attaching devices that are usually used with standard syringes. In other words, adapter hub 40 covers cannula 27 thereby converting syringe 10 into a standard Luer-type syringe. Second, adapter hub 40 and namely nozzle 43 provide a means for placing cannula 27 in fluid flow communication with these known needle hubs and attaching devices. To that end, with reference to FIG. 12, chamber 23 is in fluid flow communication with protrusion 211 which is in fluid flow communication with cannula 27, which in fluid flow communication with nozzle 43 of adapter hub 40, and nozzle 43 is in fluid flow communication with hub 51 and finally needle 52.

Figure 13C:
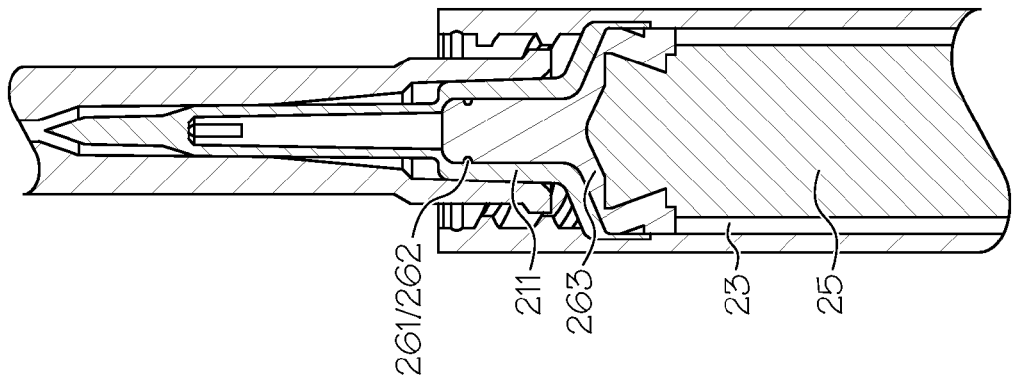
FIGS. 13A-13C are sectional views of the present syringe assembly, showing another aspect thereof.
Figure 13B:
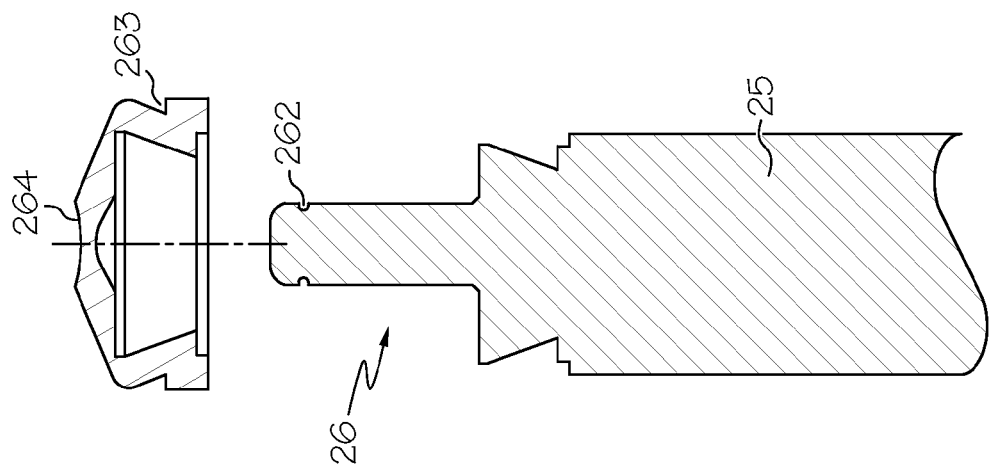
Figure 13A:
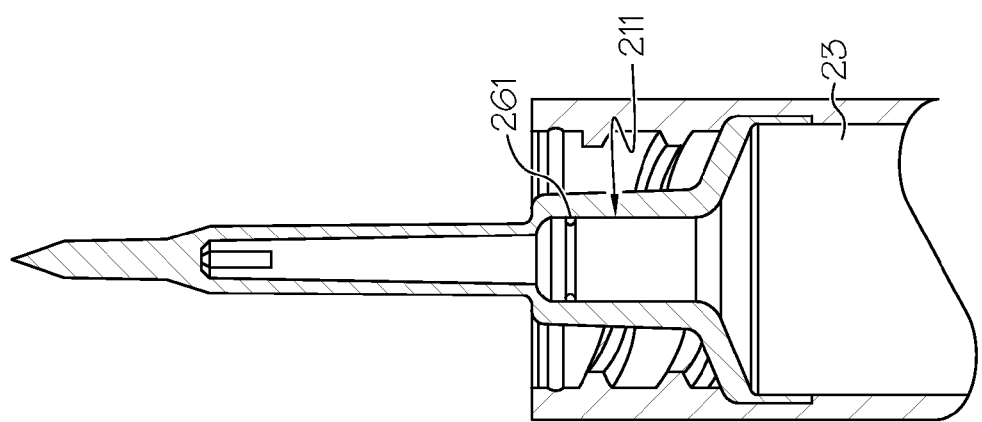

FIGS. 13A-13C show another aspect of the present invention. The interior of hollow protrusion 211 may include a circumferential notch 261 that is adapted to engage and snap-fit into a circumferential channel 262 located on the distal end of plunger tip 26. Additionally, plunger tip 26 may include a rubber plunger cover 263 having an aperture 264 which is received on the distal end of plunger tip 26. These features allow a user to permanently disable the functionality of the syringe after a single use by locking the plunger tip 26 into protrusion 211 after completion of a given medicine delivery task. Locking of the notch 261 into channel 262 is accomplished by compressing the finger guard 24 and plunger rod 25 simultaneously with intentional force after the plunger rod 25 has completely emptied the contents of chamber 23, which force causes flexible cover 263 to compress, allowing channel 262 to displace over notch 261. This functionality allows chamber 23 and protrusion 211 to completely empty while also assuring that the plunger tip 26 cannot dislodge from protrusion 211 after use. This eliminates the re-use of contaminated syringes and prevents any residual medicine or bodily fluids from exiting the syringe, therefore preventing the spread of contagious viruses and diseases including HIV and hepatitis. In some embodiments, the locking feature occurs automatically upon fully displacing the plunger, but in other embodiments, locking is achieved by applying intentional force as described above. Also, it will be appreciated that while in the above embodiment the notch 261 is located inside the hollow protrusion 211 and the channel is on the distal end of the plunger tip 26, the reverse may be true, i.e. hollow protrusion 211 may have the channel and plunger tip 26 may have the notch.

It should be understood that although the foregoing discussion contemplates that the barrel 20 and adapter hub 40 of the present invention are designed to receive injection-needle hubs, other hubs having a variety of working ends are equally compatible therewith. With regards to a typical hypodermic medicine delivery procedure, syringe 10 is intended to provide a complete solution that does not require a large bore draw needle. For example, if a technician wishes to inject a patient with a liquid medicine contained in a vial having a pre-slit (or non pre-slit) septum, the technician would first insert cannula 27 of syringe 10 into the vial, then draw plunger 25 outward which draws the medicine into orifice 29, through cannula 27 and into chamber 23. Then, the technician can attach needle hub 30 (having a needle 32 of desired gauge) to receiving collar 212, then immediately carry out the injection. Thus, what was previously a multi-step procedure (requiring the technician to attach an unsafe draw-needle hub, remove it, replace it with an injection-needle hub, then carry out the injection) has become a simple three-step process: fill the syringe via the integrated cannula, attach the hypodermic needle hub, and inject. The elimination of the draw needle greatly improves safety, sterility, and usability at a substantially reduced cost.

Likewise, port access to IV, catheter and injection receptacles is greatly simplified and much safer through the use of syringe 10. A technician no longer has to locate a draw needle hub, fill the syringe with medicine from a vial (or other source) by way of the draw needle, then remove the draw-needle hub and attach a separate needleless or needle access hub. Rather, the technician can simply insert cannula 27 into the septum or seal of the medicine vile (See FIGS. 8A-8C), fill chamber 23, then immediately provide cannula 27 into the desired access port. This procedure is simply safer and more cost-effective in comparison to existing systems and protocols which require a steel draw needle.

It is appreciated that the components of the present invention can be comprised of materials generally known utilized in the art, like hardened plastic polymers such as polypropylene, polyethylene, or polycarbonate. In some embodiments, it is desirous for cannula 27 to be comprised of a substantially rigid and hard plastic, such as polycarbonate, so that cannula 27 can access a variety of structures including pre-slit and non-slit rubber septums and other injection sites. In some embodiments, barrel 20 may be comprised of a relatively softer, less expensive material such as polypropylene, while cannula 27 is comprised of the substantially harder polycarbonate. Of course, the entirety of syringe 10 could be comprised of the harder polycarbonate, but it would likely be more expensive than if only the cannula 27 was polycarbonate. In any event, cannula 27 is integrated and contiguous with barrel 20, and therefore in the case where the materials are different, cannula 27 is fused and/or molded to barrel 20 (at protrusion 211) using manufacturing processes known in the art.

The instant invention has been shown and described herein in what is considered to be the most practical and preferred embodiments. It is recognized, however, that departures may be made therefrom within the scope of the invention and that obvious modifications will occur to a person skilled in the art.

What is claimed is:

1. A syringe assembly, comprising:
   a tubular barrel having an open proximal end, a distal end, and an internal surface delimiting a fluid retaining chamber;
   a cannula extending from and integrated with said distal end of said barrel, said cannula in fluid flow communication with said chamber;
   said cannula including a closed distal tip and a transverse orifice in fluid flow communication with said chamber of said barrel;
   said cannula including bi-lateral fluid flow channels disposed longitudinally on either side of said cannula and distal from said orifice, said bi-lateral fluid flow channels facilitating fluid flow from said orifice across said closed distal tip;
   a receiving collar surrounding a portion of said cannula and adapted to receive an attachment hub; and
   a plunger slidingly received in said chamber and configured to draw fluid into said chamber and to expel fluid out of said chamber.

2. The syringe assembly of claim 1, wherein said distal tip of said cannula is spiked to penetrate a seal of a medical access point.

3. The syringe assembly of claim 2, wherein said seal comprises a septum.

4. The syringe assembly of claim 3, wherein said septum is pre-slit.

5. The syringe assembly of claim 1, wherein said barrel further includes a hollow protrusion extending from said distal end of said barrel, said protrusion delimiting a base for said cannula and said protrusion in fluid flow communication with said chamber and said cannula.

6. The syringe assembly of claim 1, wherein said receiving collar includes at least one male thread adapted to releasably engage a proximal flange of said attachment hub.

7. The syringe of claim 6, said attachment hub including a nozzle extending distally from said flange, and a shield disposed around at least a portion of said nozzle, wherein an internal space of said nozzle is configured to receive said cannula, said nozzle in fluid flow communication with said cannula.

8. The syringe of claim 7, wherein an internal surface of said shield delimits a secondary receiving collar adapted to receive a secondary attachment hub.

9. The syringe assembly of claim 1, said attachment hub including an internal cavity and a distal aperture, said internal cavity configured to matingly receive said cannula, said cannula in fluid flow communication with said cavity and said distal aperture.

10. The syringe assembly of claim 9, wherein said distal aperture of said hub receives a hollow needle, said needle in fluid flow communication with said aperture.

11. The syringe assembly of claim 10, wherein an outer surface of said hub includes one or more longitudinal fins which facilitate manual attachment and detachment of said hub from said receiving collar.

12. A syringe assembly, comprising:
   a tubular barrel having an open proximal end, a distal end, and an internal surface delimiting a fluid retaining chamber;
   a plunger slidingly received in said chamber and configured to draw fluid into said chamber and to expel fluid out of said chamber;
   a cannula extending from and integrated with said distal end of said barrel, said cannula including a closed spiked tip, a transverse orifice, and bi-lateral fluid flow channels disposed longitudinally on either side of said cannula and distal from said orifice;
   a receiving collar including one or more male threads and surrounding a portion of said cannula;
   said cannula in fluid flow communication with said chamber, said orifice in fluid flow communication with said cannula, and said bi-lateral fluid flow channels facilitating fluid flow communication from said orifice across said closed spiked tip; and said cannula adapted to penetrate the seal of a medical access point.

13. The syringe assembly of claim 12, wherein said one or more male threads of said receiving collar are adapted to releasably engage a proximal flange of an attachment hub, said hub including an internal cavity configured to matingly receive said cannula, said cannula in fluid flow communication with said internal cavity.

14. The syringe assembly of claim 13, said internal cavity of said hub including, from a proximal end to a distal end, a proximal conical section, an intermediate conical section, a cylindrical section, and a distal tip.

15. The syringe assembly of claim 14, wherein said cannula forms a fluid-tight seal with said cylindrical section of said internal cavity of said hub.

16. The syringe assembly of claim 14, said tip including an aperture, wherein said tip receives a hollow needle, said needle in fluid flow communication with said aperture.

17. A syringe assembly, comprising:
a tubular barrel having an open proximal end, a distal end, and an internal surface delimiting a fluid retaining chamber;
a plunger slidingly received in said chamber and configured to draw fluid into said chamber and to expel fluid out of said chamber;
a hollow projection extending from and integrated with said distal end of said barrel;
a cannula extending from and integrated with said hollow projection, said cannula including a closed spiked tip, a transverse orifice, and bi-lateral fluid flow channels disposed longitudinally on either side of said cannula and distal from said orifice;
a receiving collar surrounding a portion of said hollow projection and a portion of said cannula;
said hollow projection in fluid flow communication with said chamber, said cannula in fluid flow communication with said hollow projection, said orifice in fluid flow communication with said cannula, and said bi-lateral fluid flow channels facilitating fluid flow communication from said orifice across said closed spiked tip;
said receiving collar is adapted to releasably engage an attachment hub, said hub including an internal cavity configured to matingly receive said cannula; and
said cannula adapted to penetrate the seal of a medical access point.

18. The syringe assembly of claim 17, wherein a distal end of said plunger includes a plunger tip, said tip having a rubber plunger cover and a circumferential channel, said channel adapted to engage a circumferential notch on an interior portion of said hollow protrusion when said plunger is fully inserted in said chamber, whereby said rubber plunger compresses and locks said channel around said notch.

* * * * *